United States Patent

Holick et al.

[11] Patent Number: 4,457,918
[45] Date of Patent: Jul. 3, 1984

[54] GLYCOSIDES OF VITAMINS A, E AND K

[75] Inventors: Michael F. Holick; Sally A. Holick, both of Sudbury, Mass.

[73] Assignee: The General Hospital Corporation, Boston, Mass.

[21] Appl. No.: 377,446

[22] Filed: May 12, 1982

[51] Int. Cl.$^3$ .................... A61K 31/70; C07H 15/00; C07H 15/18
[52] U.S. Cl. .................... 424/180; 536/4.1; 536/8; 536/18.1
[58] Field of Search .......... 536/4.1, 18.1, 8; 424/180

[56] References Cited

U.S. PATENT DOCUMENTS

| | | | |
|---|---|---|---|
| 2,345,098 | 3/1944 | Buxton | 424/107 |
| 2,357,172 | 8/1944 | Carlson et al. | 536/18.1 |
| 2,456,686 | 12/1948 | Doisy et al. | 260/396 R |
| 2,680,749 | 6/1954 | Cawley et al. | 549/410 |
| 2,875,195 | 2/1959 | Humphlett et al. | 544/251 |
| 3,151,127 | 9/1964 | Spanel | 549/315 |
| 4,186,207 | 1/1980 | Zeidler et al. | 424/284 |
| 4,260,602 | 4/1981 | Moreno | 424/180 |
| 4,271,196 | 6/1981 | Schmidt | 424/358 |
| 4,371,673 | 2/1983 | Pitha | 536/112 |
| 4,410,515 | 10/1983 | Holick et al. | 424/180 |

FOREIGN PATENT DOCUMENTS 2458890 6/1975 Fed. Rep. of Germany ...... 424/344

OTHER PUBLICATIONS

Hiroyuki Mima, Chemical Abstract 15938b (1964).
Pitha, Journal of the National Cancer Institute, vol. 65, No. 5 1980.
Pitha, U.S. Application, Ser. No. 17,570, filed Jul. 21, 1980 and published Mar. 27, 1981.
Friedman et al., Biochemical & Biophysical Research Communications, 70:647 (1976).
Zile et al., Proc. Natl. Acad. Sci. USA, vol. 77, No. 6, pp. 3230-3233 (Jun. 1980).
Hughes et al., Nature 268: 3047-3049 (1977).
Haussler et al., Life Sciences, vol. 18, pp. 1049-1056 (1976).
Nagubandi, Journal of Clinical Investigation, vol. 66, 1274-1280 (Dec. 1980).

Primary Examiner—Donald B. Moyer
Assistant Examiner—Shawn P. Foley
Attorney, Agent, or Firm—Saidman, Sterne & Kessler

[57] ABSTRACT

A water soluble vitamin compound of the formula selected from the group consisting of:

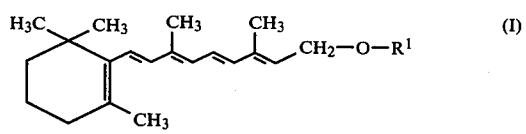

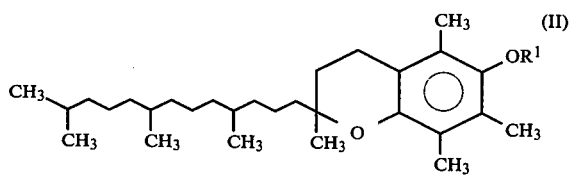

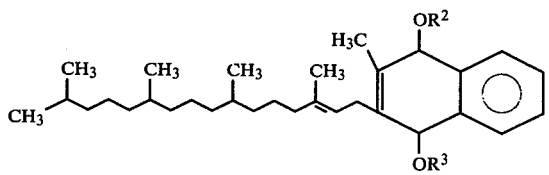

wherein $R^1$ is a straight or branched chain glycosidic residue containing 1-20 glycosidic units per residue, and $R^2$ and $R^3$ are hydrogen or $R^1$, with the proviso that at least one of $R^2$ or $R^3$ is $R^1$.

25 Claims, No Drawings

GLYCOSIDES OF VITAMINS A, E AND K

BACKGROUND OF THE INVENTION

1. Field of the Invention

The present invention relates to water-soluble glycosides of vitamins A, E and K, and their use as pharmacological agents and nutritional additives.

2. Brief Description of the Prior Art

Deficiency or excessive intake of the fat-soluble vitamins A, E and K is usually accompanied by a number of severe and prolonged diseases. Thus, for example, deficiency of vitamin A causes hyperkeratosis, xerophthalmia, keratomalacia, and night blindness, whereas hypervitaminosis of vitamin A is characterized by irritability and anorexia, weight loss, itching, fatigue, and other adverse reactions. Deficiency of vitamin E produces kwashiorkor, macrocytic and hemolytic anemia, whereas hypervitaminosis thereof causes such symptoms as skeletal muscle weakness, gastrointestinal disorders and disturbances of reproductive functions. Vitamin K deficiency causes hypoprothrombinemia.

These vitamins are therefore needed by humans and must be supplied to the body by exogenous sources, mainly vegetables. Usually vitamins are supplied by a well-balanced diet, and healthy individuals have no need to ingest extra amounts of them as medicines. In certain conditions, however, extra amounts are needed in order to cure or prevent certain of the previously mentioned deficiency syndromes.

Vitamin deficiency may result from either primary deficiencies such as inadequate diets, traumatic stresses and the like, or secondary condition deficiencies such as malabsorption (intestinal abnormality or chronic diarrhea), increased demand (during periods of pregnancy, lactation, growth and certain diseases) or reduced storage facilities (protein binding and transfer to the site of action). (See generally Korolkovas and Burkhalter "Essentials of Medicinal Chemistry," John Wiley & Sons, New York (1976), pp. 577 ff).

It has long been desired to make the fat-soluble vitamins more water-soluble so that they would be more easily absorbed by the human body. When a vitamin is relatively insoluble in an aqueous environment or in the gastrointestinal lumen, post-administration dissolution may become the rate limiting step in drug absorption. On the other hand, with water-soluble vitamins, dissolution will occur rapidly and thus facilitate transfer through the blood and to the site of activity. It would therefore be desirable to provide forms of these vitamins which are hydrophilic and/or water-soluble, yet preserve the normal biological properties of the water-insoluble drugs.

Various methods of solubilizing complex molecules are known in the prior art, but for the most part these have been unsuitable since it has also been necessary that the materials, once they are made water-soluble would be nontoxic and the solubilizing groups would be acceptable to the human system. For example, Zeidler et al, U.S. Pat. No. 4,186,207, describe the formulation of stable aqueous or aqueous alcoholic solutions of fat-soluble drugs containing hydroxyalkylester—and/or N-(hydroxyalkyl)-amide-hydroxylates. Schmidt, U.S. Pat. No. 4,271,196, describes colloidal aqueous vehicles useful for the solubilization of insoluble or slightly soluble medicaments and suitable for parenteral or local administration, by mixing the medicaments with pharmaceutical adjuvants and micelle-forming agents comprising short-chain lecithin and non-hemolytic lipids. Hiroyuki Mima, Bitamin (Kyoro) 26(1), 1–12 (1962), (also cited at Chemical Abstracts 15938b (1964)), shows the solubilization of vitamins A and D by preparing sucrose esters or raffinose esters in lieu of polyoxyethylene derivatives.

A number of specific chemical conjugates between vitamins A and E and water-solubilizing conjugative groups has been reported. Thus, Pitha (Journal of the National Cancer Institute, Vol. 65, 1011, November 1980; see also, Pitha, U.S. patent application Ser. No. 17,570, filed July 21, 1980, published Mar. 27, 1981, available through NTIA's Order No. PAT-APP L1007570), discloses water-soluble dextran-linked retinal (retinal is the aldehyde derived from vitamin A). Retinal and high molecular weight polymeric dextran (average molecular weight 40,000) conjugates were prepared, and their water solubility, as well as the water solubility of the complexes thereof with cyclodextrin were studied. Humphlett et al, U.S. Pat. No. 2,875,195, prepared aminoacid conjugates of vitamins A, $B_2$, $D_2$ and E by reacting the water-insoluble vitamins with an isocyanato ester and then hydrolyzing with a suitable basic material. When taken internally, the normal hydrolytic cleavage of the solubilized vitamin results in aminoacids which are acceptable to the human system. Cawley et al, U.S. Pat. No. 2,680,749, describe water-soluble vitamin E-active polyethylene glycol esters of tocopheryl acid esters via esterification of tocopheryl acid esters with polyethylene glycol. Spanel, U.S. Pat. No. 3,151,127, describes vitamin E conjugates with ascorbate, which are water-soluble and suitable for oral administration and parenteral injections.

A number of water-soluble principles having vitamin D activity have been extracted from various plants such as *Solanum malacoxylon* and *Cestrum diurnum* (see for example Haussler, M. R. et al, Life Sciences, Vol. 18, 1049–1056 (1956), Napoli, J. L. et al, The Journal of Biological Chemistry, 252:2580–2583 (1977), Hughes, N. R. et al, Nature, 268:347–349 (1977), or Matsumoto, Hasimo, JC-MSU 5:4 (1977)). These principles release active (water-insoluble) 1 α,25-dihydroxy vitamin $D_3$ upon treatment with a mixture of enzymes which generally includes glycosidases. The results are consistent with the belief that they may be vitamin D glycosides. The evidence also shows that the molecular weights of the principles are considerably greater than 1,000 (Humphreys, D. J., Nature New Biology, 246:155 (1973)), implying that the principle would in that case contain more than 3 glycosidic units. In any event, no analogous natural water-soluble principles for vitamins A, E or K have been described in the literature.

A series of well-defined synthetic lower molecular weight vitamin D glycosides are described in co-pending U.S. patent application Ser. No. 249,922, filed on Apr. 1, 1981, by the present co-inventors at the U.S. Patent and Trademark Office, now U.S. Pat. No. 4,410,515, and which is in its entirety, herein incorporated by reference.

A need continues to exist for biologically active, well-defined nontoxic water-soluble preparations of vitamins A, E and K.

SUMMARY OF THE INVENTION

It is, therefore, an object of the invention to provide water-soluble forms of vitamins A, E and K.

It is another object of the invention to provide water-soluble forms of the aforementioned vitamins which are biologically active.

It is still another object of the invention to provide a pharmaceutical composition containing the aforementioned vitamins.

Yet another object of the invention is to provide a method for the treatment of hypovitaminosis of any of vitamins A, E and K by using the aforementioned water-soluble forms of these vitamins.

These and other objects of the invention, as will hereinafter become readily apparent, have been attained by providing:

A water soluble vitamin compound of the formula selected from the group consisting of I, II, and III:

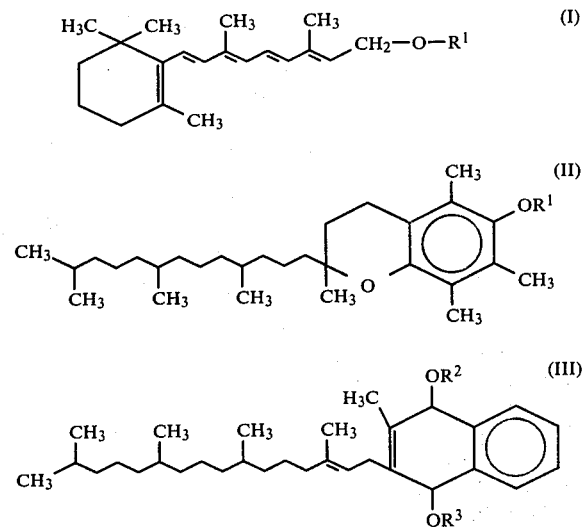

wherein $R^1$ is a straight- or branched-chain glycosidic residue containing 1-20 glycosidic units per residue; and $R^2$ and $R^3$ are hydrogen or $R^1$, with the proviso that at least one of said $R^2$ or $R^3$ is $R^1$.

DESCRIPTION OF THE PREFERRED EMBODIMENTS

The present invention provides for the first time well-defined, synthetic, water-soluble forms of vitamins A, E and K, having the formula I, II or III, as follows:

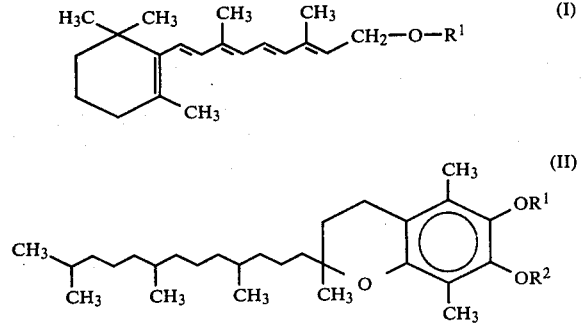

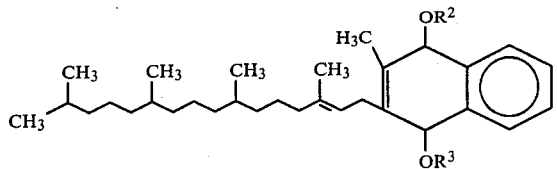

$R^1$, $R^2$ and $R^3$ are as defined supra.

It is noted that the naturally occurring vitamin A (I), is the all trans compound.

It is also to be noted that III represents the hydroquinone (or dihydroquinone) forms of vitamin K. This form can be prepared, for example, by following the methods of U.S. Pat. No. 2,456,680 to Doisy et al, which is herein incorporated by reference. Various diesters or diethers of the vitamin K hydroquinone are described in the Doisy et al patent. In addition, it is known Friedman, et al, Biochem. Biophys. Res. Comm. 70:647 (1976) that the hydroquinone of vitamin K is the biologically active product. Therefore, by providing the glycosidic mono- or di-derivatives of the hydroquinone of vitamin K, the present invention provides a direct precursor of the biologically active compound.

By glycosidic units are meant glycopyranosyl or glycofuranosyl, as well as their amino sugar derivatives. The residues may be homopolymers, random, or alternating or block copolymers thereof. The glycosidic units have free hydroxy groups, or hydroxy groups acylated with a group

wherein $R^4$ is hydrogen, lower alkyl, aryl or aralkyl. Preferably $R^4$ is $C_1$-$C_6$ alkyl, most preferably acetyl or propionyl; phenyl, nitrophenyl, halophenyl, lower alkyl-substituted phenyl, lower alkoxy substituted phenyl, and the like; or benzyl, nitrobenzyl, halobenzyl, lower alkyl-substituted benzyl, lower alkoxy-substituted benzyl, and the like.

In the case of formula III, the compounds of the invention contain at least one glycosidic residue at one of the two phenolic positions. These compounds may, however, contain two such glycosidic residues simultaneously.

The glycosides can comprise up to 20 glycosidic units. Preferred, however, are those having less than 10, most preferred, those having 3 or less than 3 glycosidic units. Specific examples are those containing 1 or 2 glycosidic units in the glycoside residue.

The glycopyranose or glycofuranose rings or amino derivatives thereof may be fully or partially acylated, or completely deacylated. The completely or partially acylated glycosides are useful as defined intermediates for the synthesis of the deacylated materials.

Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N-acetylneuraminic acid, D-glucosamine, lyxosylamine, D-galactosamine, and the like.

When more than one glycosidic unit is present on a single hydroxy group (i.e., di- or polyglycosidic residues), the individual glycosidic rings may be bonded by 1-1, 1-2, 1-3, 1-4, 1-5 or 1-6 bonds, most preferably 1-2, 1-4 and 1-6. The linkages between individual glycosidic rings may be α or β.

Specific examples of compounds of the invention are the vitamin A, E and K (hydroquinone or dihydroquinone) conjugates of:

(β-D-glucopyranoside);
(β-D-fructofuranoside);
(β-cellobioside);
(β-maltoside);
(β-lactoside);
(β-trehaloside);
raffinoside; and
gentiobioside.

The glycosidic derivatives of the vitamins of the present invention can be prepared by standard synthetic methods well known to those skilled in the art. The vitamin is treated with silver trifluoromethanesulfonate (AgTFMS) in a refluxing solution of an inert nonpolar solvent such as benzene, toluene or CH$_2$Cl$_2$ to which is added a fully acylated glycoside or fully acylated straight or branched chain glycosidic polymer, either of these containing an appropriate leaving group (L.G.) at position C-1' of the terminal ring (or on the single ring, as called for). Condensation occurs according to the following reaction, indicated here for a single glycoside for purpose of illustration only:

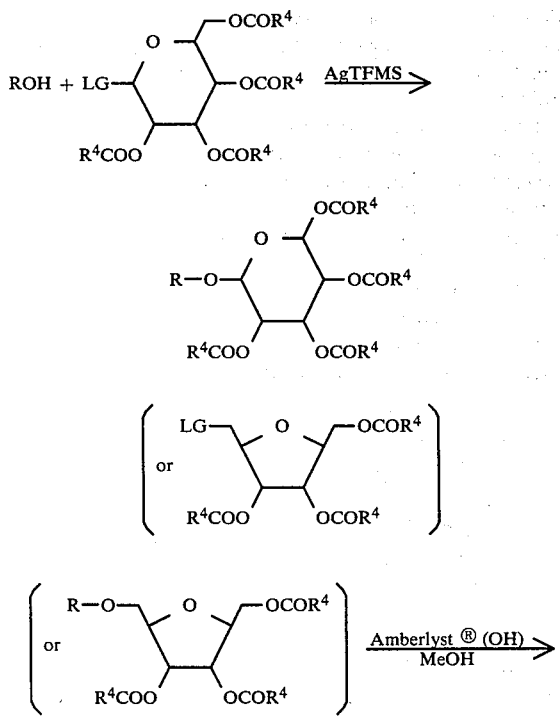

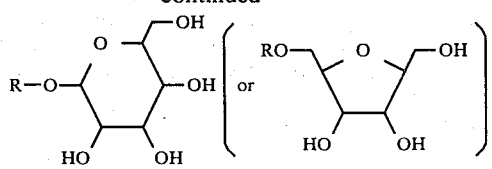

In this reaction sequence, R is any of the alcoholic radicals of I, II or III, supra, R$^4$ is as defined previously, LG is a common leaving group such as bromine, chlorine, iodine, p-toluenesulfonyl, and the like, capable of being replaced in a bimolecular nucleophilic substitution reaction.

When the vitamins are reacted with a glycosidic polymer, one or more of the OCOR$^4$ groups in the glycopyranoside or glycofuranoside rings is replaced by a fully acylated glycosidic unit, with the proviso that the total number of glycosidic units not exceed 20.

The reaction is carried out at from room temperature to refluxing conditions for a period of 1-10 hours, and is thereafter cooled and filtered to remove the silver salt. The filtrate is dried and the inert solvent is evaporated. The resulting product can be purified by any of the standard modern purification methods such as high performance liquid chromatography, silicic acid chromatography, thin layer preparative chromatography, and the like.

After separation of the individual products, the glycosidic residues are deacylated in base, such as sodium methoxide in methanol, ammonia in methanol, or Amberlyst® A-26(OH) in methanol. Further purification by high performance chromatography is usually indicated to obtain the highly purified product.

When the starting vitamin is the dihydroquinone of Vitamin K, i.e. it carries two hydroxy groups, one of these may need to be selectively protected with a protecting group which can be ultimately removed after the condensation, and before, during or after the deacylation of the glycosidic residues. The selective protection of phenolic hydroxy groups in the starting materials can be carried out by using standard protection and deprotection reactions, well known to those skilled in Organic Chemistry. Once the desired protected vitamin K derivative is prepared, the same is reacted with silver carbonate or silver TFMS or other methods for coupling (as described e.g. by Igarashi, K., in "Advances in Carbohydrate Chemistry and Biochemistry," Vol 34 243-283, or Warren, C. D. et al, Carbohydrate Research, 82: 71-83 (1980)), and the glycosidic or polyglycosidic residue as in scheme I above, followed by deacylation, deprotection and purification.

The acylated glycoside containing a leaving group at position C-1' of the first (or only) glycosidic ring can be prepared, for example, by the methods of Fletcher, H. G., Jr., "Methods in Carbohydrate Chemistry" 2: 228 (1963), or Bonner, W. A., Journal of Organic Chemistry 26: 908-911 (1961), or Lemieux, R. U. "Methods in Carbohydrate Chemistry", Vol. II, 221-222.

Oligosaccharide intermediates can be prepared, for example, by the methods of Lemieux, R. U., J. of Amer. Chem. Soc. 97: 4063-4069 (1975); or Frechet, J. M. J., "Polymer-Supported Reactions in Organic Synthesis" (1980) 407-434, or Kennedy, J. F., "Carbohydrate Chemistry" 7: 496-585 (1975).

Commercially available sugars include (Pfanstiehl Laboratories, Inc): Pentoses, such as: D-Arabinose, L-Arabinose, D-Lyxose, L-Lyxose, R-Ribose, D-Xylose, L-Xylose; Hexoses, such as: Dextroses, D-Fructose, D-Galactose, α-D-Glucose, β-D-Glucose, L-Glucose, Levulose, D-Mannose, L-Mannose, L-Sorbose; Heptoses, such as: D-Glucoheptose, D-Mannoheptulose, Sedoheptulosan; Disaccharides, such as: Cellobiose, 3-O- β-D-Galactopyranosyl-D-arabinose, Gentiobiose, Lactoses, α-Lactulose, Maltose, α-Melibiose, Sucrose, Trehalose, Turanose; Trisaccharides, such as: Melezitose, Raffinose; Tetrasaccharides, such as: Stachyose, Polysaccharides and derivatives, such as: Arabic Acid, Chitin, Chitosan, Dextrin, Cyclo-Dextrins, Glycogen, Inulin.

When the vitamin glycosides of the invention are used in the treatment of hypovitaminosis states, in an animal, especially in a human, the endogenous glycosidase enzymes of the animal directly release the active form of the vitamin, and an easily metaboliseable sugar.

The water-soluble glycosilated vitamin conjugates of the present invention include hydrophilic derivatives of good water solubility to derivatives of excellent water solubility. They can be used generally in any application where the use of vitamin A, E or K has been called for in the prior art. The advantage of the conjugates of the invention resides in their water-solubility and thus their ease of administration in aqueous media such as, for example, saline or aqueous buffers. This allows the utilization of these conjugates in such devices as vitamin releasing in-line pumps, intravenous dispensation and the like.

The conjugates of the invention can be administered by any means that reverses hypovitaminosis of vitamins A, E or K; or maintains physiological levels of these vitamins in animals, especially humans. For example, administration can be topical, parenteral, subcutaneous, intradermal, intravenous, intramuscular, or interperitoneal. Alternatively or concurrently, administration can be by the oral route. The dosage administered will be dependent upon the age, health and weight of the recipient, kind of concurrent treatment if any, frequency of treatment, and the nature of the effect desired. Generally, a dosage of active ingredient compounds will be from about 0.1 μg to 10 mg per kg of body weight. Normally, from 0.1 μg to 100 μg per kg per application, in one or more applications per therapy, is effective to obtain the desired result.

The compounds can be employed in dosage forms such as tablets, capsules, powder packets or liquid solutions, suspensions or elixirs for oral administration, or sterile liquids for formulations such as solutions or suspensions for parenteral use. In such compositions, the active ingredient will ordinarily always be present in an amount of at least $1 \times 10^{-6}\%$ by wt. based upon the total weight of a composition, and not more than 90% by wt. An inert pharmaceutically acceptable carrier is preferably used. Among such carriers are 95% ethanol, vegetable oils, propylene glycols, saline buffers, etc.

Having now generally described this invention, a more complete understanding can be obtained by reference to an Example, which is included herein for purposes of ilustration only and is not intended to be limiting unless otherwise specified.

EXAMPLE

The Glycosides of vitamin A, (retinol), vitamin E (tocopherol) and hydroquinone form of vitamin K can be prepared as follows:
Coupling Reaction The coupling of retinol or tocopherol or of the hydroquinone form of vitamin K to an activated glycoside can be carried out according to the procedure of Warren, C. D. et al: Carbohydrate Research. 82:71, 1980. To a solution of vitamin K hydroquinone, retinol or tocopherol (1 mmole) in dry dichloromethane (5 ml) in the dark can be added silver triflate (2 mmole, Aldrich Chemical Co., Milwaukee, WI 53233), 2,4,6-trimethylpyridine (2 mmole), and a solution of the glycoside (2 mmole) in dichloromethane (5 ml). (An example of an appropriate glycoside is acetobromoglucose, prepared according to the procedure of Lemieux, R. V.: In, Methods of Carbohydrate Chemistry, Vol. II. R. L. Whistler and M. L. Wolfrom, eds. Academic Press. p. 221, 1963.) The suspension can be stirred in the dark under nitrogen for 2 h at 0° and then at room temperature. The reaction can be followed by thin-layer chromatography, and when complete, can be diluted with dichloromethane and filtered through glass wool. The filtrate can be successively washed with water, 0.1 M sulfuric acid, a saturated solution of potassium hydrogen carbonate, and water, and coevaporated with absolute ethanol under nitrogen. The resulting products (the major product having the β- glycoside linkage) can be isolated and purified by high-pressure liquid chromatography.

Deacetylation

The product can be deacetylated according to the procedure of Reed, L. A. et al: J.C.S. Chemical Communications. p. 760, 1981. (This procedure, in contrast to the classical Zemplen procedure, will avoid the problem of the removal of the ionic salts which accompany deacetylation.) For example, the glycoside of retinol or tocopherol can be stirred in methanol solution at room temperature with a catalytic amount (150 g of the moist resin per milligram of glycoside) of the macroreticular Amberlyst A-26 (OH) (Rohm and Haas, Philadelphia, Pa. 19105). The reaction can be followed by high-pressure liquid chromatography. Isolation of the product can be accomplished by filtration and evaporation of the filtrate.

Having now fully described this invention, it will be apparent to those of skill in the art that the same can be performed within a wide and equivalent range of parameters, structures and compositions without affecting the spirit or scope of the invention or any embodiment thereof.

What is claimed as new and intended to be covered by Letters Patent of the United States is:

1. A water soluble vitamin compound of the formula selected from the group consisting of:

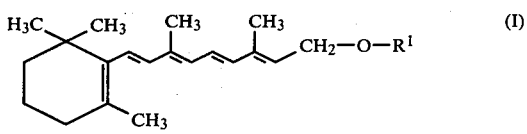

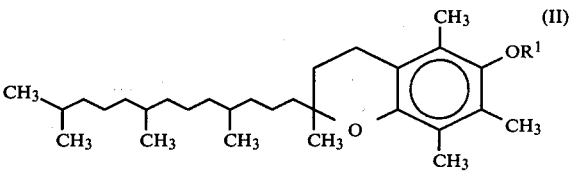

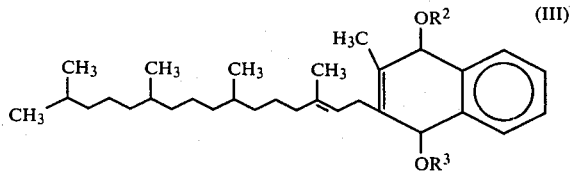

wherein R¹ is a straight or branched chain glycosidic residue containing 1–20 glycosidic units per residue, and R² and R³ are hydrogen or R¹, with the proviso that at least one of said R² or R³ is R¹.

2. The compound of claim 1 wherein said glycosidic residue has 1–10 units per residue.

3. The compound of claim 1 wherein said glycosidic residue has 1, 2 or 3 glycosidic units per residue.

4. The compound of claim 3 wherein said glycosidic residue contains 1 glycosidic unit.

5. The compound of claim 3 wherein said glycosidic residue contains 2 glycosidic units.

6. The compound of claim 3 wherein said glycosidic residue contains 3 glycosidic units.

7. The compound of claim 1 which is

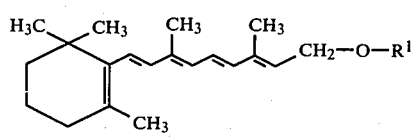

8. The compound of claim 7 wherein said glycosidic residue has 1, 2 or 3 glycosidic units.

9. The compound of claim 1 which is

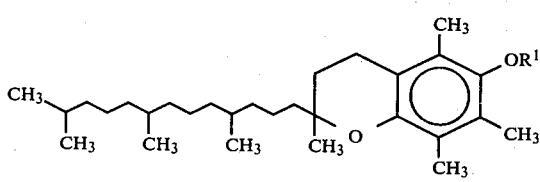

10. The compound of claim 9 wherein said glycosidic residue has 1, 2 or 3 glycosidic units.

11. The compound of claim 1 which is

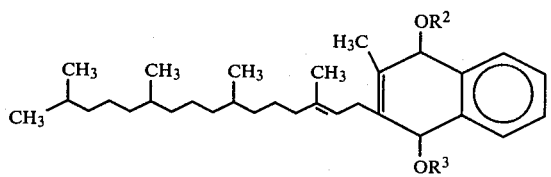

12. The compound of claim 11 wherein said glycosidic residue has 1, 2 or 3 glycosidic units.

13. The compound of any of claims 11 or 12 wherein R² is hydrogen and R³ is R¹.

14. The compound of any of claims 11 or 12 wherein R³ is hydrogen and R² is R¹.

15. The compound of any of claims 11 or 12 wherein both R² and R³ are R¹.

16. A method of treating vitamin A hypovitaminosis in a mammal having endogenous glycosidase enzymes which comprises administering to said mammal a compound according to formula (I) of claim 1, in an amount sufficient to reverse said hypovitaminosis.

17. A method of treating vitamin E hypovitaminosis in a mammal having endogenous glycosidase enzymes which comprises administering to said mammal a compound according to formula (II) of claim 1, in an amount sufficient to reverse said hypovitaminosis.

18. A method of treating vitamin K hypovitaminosis in a mammal having endogenous glycosidase enzymes which comprises administering to said mammal a compound according to formula (III) of claim 1, in an amount sufficient to reverse said hypovitaminosis.

19. The method of claims 16, 17 or 18, wherein said administration is parenteral.

20. The method of claims 16, 17 or 18, wherein said administration is subcutaneous.

21. The method of claims 16, 17 or 18, wherein said administration is intradermal.

22. The method of claims 16, 17 or 18, wherein said administration is intravenous.

23. The method of claims 16, 17 or 18, wherein said administration is intramuscular.

24. The method of claims 16, 17 or 18, wherein said administration is intraperitoneal.

25. The method of claims 16, 17 or 18, wherein said administration is oral.

* * * * *